United States Patent
Stroganov et al.

(10) Patent No.: US 9,631,229 B2
(45) Date of Patent: Apr. 25, 2017

(54) METHOD OF NUCLEIC ACIDS ANALYSIS BY REAL-TIME POLYMERASE CHAIN REACTION AND DEVICE FOR PERFORMING THE SAME

(75) Inventors: Alexander Anatolevich Stroganov, St. Petersburg (RU); Maxim Nikolaevich Slyadnev, St. Petersburg (RU)

(73) Assignee: Lumex Instruments Limited, Nicosia (CY)

(*) Notice: Subject to any disclaimer, the term of this patent is extended or adjusted under 35 U.S.C. 154(b) by 316 days.

(21) Appl. No.: 13/122,484

(22) PCT Filed: Oct. 8, 2009

(86) PCT No.: PCT/RU2009/000531
§ 371 (c)(1),
(2), (4) Date: Apr. 4, 2011

(87) PCT Pub. No.: WO2010/047619
PCT Pub. Date: Apr. 29, 2010

(65) Prior Publication Data
US 2011/0189683 A1 Aug. 4, 2011

(30) Foreign Application Priority Data
Oct. 23, 2008 (RU) .................. 2008143309

(51) Int. Cl.
C12Q 1/68 (2006.01)
C12P 19/34 (2006.01)
C12M 1/00 (2006.01)
C12M 1/34 (2006.01)

(52) U.S. Cl.
CPC .................. C12Q 1/6844 (2013.01)

(58) Field of Classification Search
None
See application file for complete search history.

(56) References Cited

U.S. PATENT DOCUMENTS

| | | | |
|---|---|---|---|
| 6,153,412 A | 11/2000 | Park et al. | |
| 6,524,830 B2 | 2/2003 | Kopf-Sill | |
| 6,660,517 B1 | 12/2003 | Wilding et al. | |
| 6,664,044 B1 | 12/2003 | Sato | |
| 7,118,910 B2 | 10/2006 | Unger et al. | |
| 7,122,799 B2* | 10/2006 | Hsieh et al. | 250/339.12 |
| 7,264,950 B1* | 9/2007 | Lee et al. | 435/91.2 |
| 2007/0196237 A1 | 8/2007 | Neuzil et al. | |
| 2007/0254284 A1* | 11/2007 | Zhao | 435/6 |
| 2008/0214412 A1 | 9/2008 | Stahler et al. | |

FOREIGN PATENT DOCUMENTS

| | | |
|---|---|---|
| RU | 2259401 C1 | 8/2005 |
| WO | 2005103277 A1 | 11/2005 |
| WO | 2006085948 A2 | 8/2006 |

OTHER PUBLICATIONS

Fixe et al. Materials Research Society Symposium Proceedings 820: O2.8.1-O2.8.6 (2004).*
Elgort et al. Clinical Chemistry (2004) 50(10): 1817-1819.*
Kopp, et al.; "Chemical Amplification: Continuous-Flow PCR on a Chip", Science, May 15, 1998, pp. 1046-1048, vol. 280.
Matsubara, Yasutaka et al., "Application of a Microchamber array for DNA Amplification Using a Novel Dispensing Method," Arch. Histol. Cytol., 2002, v. 65, n. 5, p. 481-488.
Zhang, Chunsun et al., "Miniaturized PCR Chips for Nucleic Acid Amplification and Analysis: Latest Advances and Future Trends", Nucleic Acids Research, 2007, v. 35, n. 13, 4223-4237.
Slaydanev, M.N. et al., "A Detection System for Microfluidic Chips Based on Epifluorescence Videomicroscopy and it's Analytical Potentials", Journal of Analytical Chemistry, 2005, v. 60, n. 4, p. 317-324.
Morrison, Tom, et al., "Nanoliter High Throughput Quantitative PCR", Nucleic Acids Research, 2006, v. 34, p. e123.
Matsubara Yasutaka et al., "Microchamber Array Based DNA Quantification and Specific Sequence Detection from a Single Copy via PCR in Nanoliter Volumes", Biosensors and Bioelectronics, 2005, v. 20, n. 8, p. 1482-1490.
Chien, Chao-Heng et al., "The Design and Fabrication of Polymerase Chain Reaction Platform", Microsyst Technol, 2007, v. 13: 1523-1527.
Higgins, James A., et al., "A Handheld Real Time Thermal Cycler for Bacterial Pathogen Detection", Biosensors and Bioelectronics, 2003, v. 18, n. 9, pp. 1115-1123; abstract only.
Lee Da-Sheng, et al., "Development of a CCD-Based Fluorimeter for Real-Time PCR MAchine", Sensors and Actuators B: Chemical, 2005, v. 107, n. 2, pp. 872-881; abstract only.
Kricka, L.J., et al., "Microchip PCR", Anal Bioanal Chem, 2003, v. 377, p. 820-825.

* cited by examiner

*Primary Examiner* — Young J Kim
(74) *Attorney, Agent, or Firm* — Walker & Jocke

(57) ABSTRACT

With respect to molecular biology, medicine, and biotechnology, provided is a method related to the performance of Polymerase Chain Reaction. The method includes using the device for identification of nucleic acids containing a microchip with at least one reaction zone on its surface. The microchip contains a heat-conducting substrate made of aluminum while each reaction zone is separated from the heat-conducting substrate by a layer of the passivating material covalently bound to the surface of the heat-conducting substrate while over the layer of the passivating material one or several dried components of the polymerase chain reaction is placed. In this method the ratio of the aggregate thermal mass of the microchip to thermal conductance of the microchip substrate does not exceeding 0.04 s. The technical result is reduced duration of the analysis, higher reliability, accuracy, efficiency and cost-effectiveness of the analysis.

31 Claims, 5 Drawing Sheets

METHOD OF NUCLEIC ACIDS ANALYSIS BY REAL-TIME POLYMERASE CHAIN REACTION AND DEVICE FOR PERFORMING THE SAME

CROSS-REFERENCE TO RELATED APPLICATIONS

This application is a national stage entry of PCT/RU2009/000531. This application claims priority to PCT/RU2009/000531, filed Apr. 4, 2011, which claims priority to Russian Patent Application No. 2008143309, filed Oct. 23, 2008, the disclosures of each of which are incorporated herein by reference in its entirety.

TECHNICAL FIELD

The application refers to molecular biology, medicine, biotechnology and is related to performance of Polymerase Chain Reaction (PCR) and device for its implementation with real-time registration of reaction-product build-up (real-time PCR, rt-PCR). The proposed method and device can be used in medicine, veterinary, food processing, in environmental researches and in other fields related to detection, identification and quantitative evaluation of nucleic acids in the samples under investigation.

The PCR represents multiple repeated cycles of synthesis of a specific DNA fragment (amplification) caused by cyclic changes of the temperature of the reaction mixture and resulting in exponential increase in the quantities of the DNA fragment limited by two oligonucleotide primers. The cyclic change of the temperature of the reaction mixture known to specialists in the field as thermocycling undergoes through the following consecutive stages: denaturation of the double stranded target DNA molecule (melting), attachment of oligonucleotide primers to complementary sites of the formed single stranded target DNA molecules (annealing) and elongation of the primers with the participation of the thermostable polymerase until elongated fragments of complementary DNA molecules are formed (elongation).

The PCR is used for amplification of nucleic acids and allows detection and identification of the presence and quantity of nucleic acid with the target nucleotide sequence in the DNA/RNA sample.

The PCR experiment involves preparation of a reaction mixture in a buffer solution which generally contains thermostable polymerase, deoxyonucleoside triphosphates, oligonucleotide primers, and magnesium ions. The sample of DNA under investigation is added to the mixture for further amplification with subsequent registration of the amplified nucleotide sequences (amplicons).

For real-time registration of the reaction results the reaction is performed using a thermocycler equipped with a fluorescent detector in the presence of either fluorescent intercalating dyes or fluorescently labeled primers or probes.

TERMS AND DEFINITIONS

The thermal mass of the object (J/K) equal to the thermal capacity of the material it is made of and multiplied by its mass characterizes the ability of the object under investigation to change its temperature at heat energy supply or removal. The full thermal mass of a compound object containing several parts made of different materials is equal to the sum of thermal masses of all its parts.

The thermal conductivity coefficient of the material (W/m*K) characterizes the ability of the material to conduct heat energy.

Thermal conductance of the object (W/K) equal to the product of the thermal conductivity coefficient of the material it is made of and the area of the heat exchange surface divided by the thickness of the material characterizes the ability of the object to conduct heat energy through the heat exchange surface.

The thermal diffusivity coefficient ($m^2/s$) equal to the ratio of the material thermal conductivity to the product of its thermal capacity by its density characterizes the ability of the material for heat exchange with the surrounding medium relative to the process of heat accumulation in the material itself.

The following characteristic is true for a system containing two objects: the first object that is heated or cooled and the second object through which the heat is exchanged. The ratio of the thermal mass of the first object to the thermal conductance of the second object expressed in seconds characterizes the ability of the system to quickly supply heat to the first object through the second one and remove heat from the first object through the second one.

BACKGROUND ART

The existing PCR methods using commercially available equipment are generally based on utilization of polymer tubes that are installed in metallic heating blocks. The high thermal mass of standard heating blocks with tubes installed in them and samples, the low thermal conductivity of the walls of the tubes restrict heating and cooling rates of the sample and may lead to high temperature non-uniformity across the sample in the tube.

When using usual laboratory devices intended for PCR in polymer tubes or plates the recommended time of maintaining the temperature during thermal cycling is 2 minutes or more. Ausubel et al., eds. (1996) Current Protocols in Molecular Biology, Current Protocols, Greene Publishing Associates, Inc. and John Wiley & Sons, Inc., for example, recommend using a five-minute duration per cycle excluding time for temperature transitions. As a result, the PCR analysis consisting of 40 thermal cycles would take 3 or more hours to be completed using typical PCR equipment with 20-50 µL sample volume.

In order to decrease the time spent on one cycle there have been recently proposed many methods of PCR analysis in miniature reaction containers. To increase the time required for temperature transition for the mass of the heating element, the mass of the containers and the volume of the samples in such devices have been considerably decreased, which allowed reduction of the thermal mass, use of materials with high thermal conductivity coefficients and a higher ratio of the sample surface area to its volume. Methods of contactless heat supply to the sample are also used for heating. For example, RapidCycler (Idaho Technologies Inc., USA) allows a relatively fast change of the PCR mixture temperature during temperature transition and ensures a relatively effective heat transfer from the heater to the samples. In this device 30 cycles of rt-PCR may be completed within 10 minutes.

There are also methods implemented in microfluidic devices that reduce the time required for one cycle. Kopp et al. (1998) Science, 280:1046, for example, describes a device where the PCR mixture successively flows through a microchannel in the form of a meander in the microfluidic chip through three temperature zones, which results in cyclic change of the PCR temperature during 20 thermal cycles. As the cross-section of the microchannel is relatively small, the temperature of the solution inside the microchannel is set rather fast. The time during which the mixture is at a certain temperature is regulated in this case by the flow rate. The authors demonstrated the possibility of PCR in the described device with the cycle time of 6.6 seconds.

Thus, application of microchip technologies allows significant decrease in the PCR cycling time, which leads to decrease of the total PCR analysis time and increased throughput.

However, rt-PCR implementation in such microfluidic devices faces with certain difficulties.

The higher ratio of the surface area between the microreactor and the sample to the volume leads to decrease of polymerase activity and even to irreversible inactivation of the enzyme. The surfaces of such materials as silicon, metals, quartz, and glass demonstrate irreversible sorption of DNA and enzyme, as well as other components of the reaction. To eliminate the restrictions it is necessary to add substances that prevent sorption and deactivation of PCR components, such as amino acids, peptides and surfactants, into reaction mixture [U.S. Pat. No. 6,660,517 "Mesoscale polynucleotide amplification devices"]. The same patent also displays some methods that allow PCR microreactor surface passivation. Such protection layers prevent adsorption and inhibition of PCR components, which allows for the achievement of high sensitivity of PCR analysis.

One of the problems known to specialists in PCR analysis is evaporation of the sample during the thermocycling phase. Since temperature of DNA denaturation is close to the boiling point of water, intensive evaporation of PCR mixture during the reaction can inhibit the PCR flow, which is generally eliminated in standard devices either by insulating the mixture water surface from the atmosphere by means of a liquid immiscible with water, by mineral oil, for example, or by using a heated lid to seal the reaction vessels.

In closed channels of microfluidic chips the microreactors can be sealed with valves in the microchannel [U.S. Pat. No. 7,118,910 "Microfluidic device and methods of using the same"]. Implementation of this method of sealing is technically complicated and increases the cost of the analysis using such a microchip.

Prevention of evaporation during thermocycling for microchips containing open-well microreactors is usually achieved by insulation of the reaction mixture from the atmosphere by application of a liquid immiscible with water on the surface of the aqueous solution of the reaction mixture, mineral or silicone oil, for example [U.S. Pat. No. 6,664,044 "Method for conducting PCR protected from evaporation"]. However, in the described device an ink-jet system is repeatedly used to inject the working PCR and samples, which may lead to uncontrolled degradation of PCR reagents and internal contamination of the samples in the process of application. Another method and device [USA patent application 20070196237 "Apparatus for regulating the temperature of a biological and/or chemical sample and method of using the same"] uses a microchip with reaction volumes on the substrate surface that are a droplet of a liquid immiscible with water, with the PCR mixture placed in it. However, in this method the reaction mixture is separated from the heated substrate surface by a layer of the liquid immiscible with water, which slows down the heating and cooling process. Moreover, the reaction volumes in this method can uncontrollably move, since the entire surface of the heat-conducting substrate is hydrophobic. It may lead to spatial mismatch of the heated zone and the heated sample in the process of the sample introduction and thermal cycling, which will result in unreliable results of the PCR analysis.

Another shortcoming common for the known microfluidic devices is the increased labour intensity in mixing the samples with the PCR mixture components prior to introduction into the microchip. Besides, this procedure requires costs for additional consumables (plastic tips, tubes) and is practically unrealizable in usual tubes with the volume of the handled liquids of less than one microliter due to the increased probability of evaporation of the reagents and samples during mixing. There are methods that allow immobilization of one or several components of the reaction mixture necessary for the PCR in the microreactor to fill the microreactor with a aqueous solution containing nucleic acids and the remaining components of the PCR mixture [U.S. Pat. No. 7,118,910 "Microfluidic device and methods of using the same"]. However, this method is labour-intensive and is hard to control during production as it requires application of biological reagents directly in the process of the microchip manufacture, which increases the danger of the negative impact of subsequent technological processes on the applied reactants (impact of increased temperature, chemical compounds, emission).

There are methods that involve lyophilization of the prepared PCR mixture containing all or almost all PCR reagents and additional stabilizers in the tubes [RF patent 2259401 "Dry mixture of reagents for polymerase chain reaction and method of PCR analysis", U.S. Pat. No. 6,153,412 "Lyophilized reagent for polymerase chain reaction"]. This method can be implemented practically in any microreactor system with open reactors.

Despite the large number of available methods and devices of rt-PCR implementation in microfluidic and microchip formats there is still a high need for development of new, improved methods and devices. This technical field has a need for a cost-effective method of express quantitative identification of nucleic acids of a variety of samples having high sensitivity without large labour costs in preparation for the analysis as well as the need for a device for its implementation.

The closest analogue to an exemplary embodiment of the present application may be said to be the method and the device described in the USA patent application 20070196237 "Apparatus for regulating the temperature of a biological and/or chemical sample and method of using the same". The application discloses the method of conducting biochemical reactions, including rt-PCR, containing stages of thermocycling and fluorescent signal detection using a thermoregulation module comprising a heater and temperature detector. A substrate of a heat-conducting material is placed on the module and a biological sample is applied on the substrate, for example, a mixture containing all components for real-time PCR analysis that is insulated from the atmosphere by introducing into a virtual reaction cell formed by a liquid immiscible with water, by mineral oil, for example.

The main drawbacks of the prototype are the low real heating and cooling rates of the sample; technological complexity of the thermoregulation module with integrated microheaters and thermosensors, which results in higher costs and reduces the commercial attractiveness of the device. Another drawback of the analogue is the uncontrolled sensitivity reduction at the possible contact of the sample with the surface of the heat-conducting material. In addition, the method and device disclosed in the analogue description require preliminary preparation of the solutions of PCR components, mixing of PCR components with the sample and introduction of the resulting mixture into reaction zones, which leads to additional labour costs, higher risk of operator's errors and higher costs of analysis due to the growing quantity of consumables (tubes, tips for the dosing unit, reactants). Another drawback of the analogue is the possibility of spatial mismatch of the heated zone and the heated sample in the process of the sample introduction and thermal cycling, which will result in unreliable results of the PCR analysis.

SUMMARY

The scope of the exemplary embodiment is development of the method and device for its implementation that would allow:
1. to reduce the time of the analysis and to increase the throughput of the analysis;
2. to increase the sensitivity, accuracy and reliability of the analysis;
3. to reduce the labour costs of identification of nucleic acids by rt-PCR method;
4. to reduce the cost of PCR analysis.

The scope is achieved by using the method of identification of nucleic acids described in the exemplary embodiment by means of a real-time polymerase chain reaction and a device for rt-PCR analysis containing a microchip.

The proposed method involves identification of nucleic acids by means of a real-time polymerase chain reaction including the following stages:
introduction of liquid samples containing nucleic acid into the reaction zones on the upper surface of the heat-conducting substrate and insulation of the introduced samples from the atmosphere;
interaction of the nucleic acid of the sample with the components of the polymerase chain reaction during thermal cycling of the samples with heat removal through the external surface of the microchip;
fluorescent identification of the change of the quantity of the polymerase chain reaction products in the process of thermal cycling;
identification of the quantity of the initial nucleic acid in the samples by the dynamics of growth of the fluorescent signal.

The microchip is fabricated with a heat-conducting substrate made of a heat-conducting material with the thermal conductivity coefficient higher than 1 W/cm·K and with thermal diffusivity coefficient higher than 0.6 cm$^2$/s. The reaction zones on the microchip surface are separated from the heat-conducting substrate by a layer of a passivating material covalently bound to the surface of the heat-conducting material. The introduced samples are insulated from the atmosphere by a layer of liquid that is retained on the upper surface of the heat-conducting substrate by means of a frame; the ratio of the aggregate thermal mass of the microchip with the introduced samples and the layer of a liquid immiscible with water to thermal conductance of the microchip substrate does not exceed 0.04 s.

The device for implementation of this method contains a microchip with at least one reaction zone on its surface that is mechanically bound with the microchip holder, thermally bound with the thermal cycling block and optically bound with the fluorescent detector. The device also contains at least one radiation source optically bound with the excitation channel spectral filtration system and with the microchip. This fluorescent detector is optically bound with the microchip via the emission channel spectral filtration system while this thermal cycling block is embodied with the possibility of heating, cooling and maintaining the temperature of the microchip. The device contains a control system electrically bound with the identified detector, radiation source and thermal cycling bock.

In such a case the microchip contains a heat-conducting substrate manufactured from a material with a thermal conductivity coefficient higher than 1 W/cm·K and a thermal diffusivity coefficient higher than 0.6 cm$^2$/s. Each reaction zone on the surface of the microchip is separated from the heat-conducting substrate by a layer of a passivating material covalently bound with the surface of the heat-conducting substrate. On the upper surface of this microchip there is a frame with the possibility of retaining the assigned quantity of the liquid immiscible with water on the upper surface of the microchip, with the ratio of the aggregate thermal mass of the microchip with the introduced samples and the layer of the liquid immiscible with water to the thermal conductance of the microchip substrate does not exceed 0.04 s.

The aggregate features of the proposed invention are due to:
1) increased thermal cycling rate;
2) elimination of inhibition of the reaction by means of a protection layer of the surface of the reaction zones;
3) elimination of uncontrolled displacement of the sample relative to the reaction zone;
4) creation of a microchip containing dried PCR reagents necessary for identification of the assigned nucleic acids; and
5) reduced consumption of reagents and consumables and lower labour intensity of the analysis,
allow to fulfill the set task. The proposed exemplary embodiment uses a microchip, its substrate manufactured from materials with a thermal conductivity and thermal diffusion. The surface of the reaction zones on the upper surface of the microchip is covered with a passivating layer. The PCR mixture evaporation is prevented by a layer of insulating liquid and the microchip can also contain one or several PCR mixture components in the reaction zones.

There are various possible schemes of implementation of the method described in the exemplary embodiment.

There are several variants of interaction of the nucleic acid of the sample with PCR components. For example, before the analysis the sample containing nucleic acid is mixed with one or several components of the PCR mixture. It is also possible to mix the sample with the solution containing all the components necessary to perform the PCR analysis. It is also possible to mix the sample with the buffer solution containing one component, for example, magnesium ions $Mg^{2+}$ or several components, for example, magnesium ions $Mg^{2+}$ and polymerase, or magnesium ions $Mg^{2+}$, oligonucleotide primers, and fluorescence probes. In such cases addition of remaining components for the PCR analysis can be performed by introduction of solutions containing these components before or after introduction of the samples by any method. It is preferred that the remaining PCR components may be introduced into the reaction zones before the sample introduction.

It is even more advantageous that the PCR components be introduced into the reaction zones in dried form before introduction of the samples. To achieve this, one or more PCR components in the form of an aqueous solution can be placed into the reaction zones on the microchip surface on the layer of the passivating material and the solution should be dried. This method supposes that the PCR components, such as deoxyonucleoside triphosphates, forward and reverse oligonucleotide primers, probes with fluorescent labels should be introduced into the reaction zones and dried out. It is even more preferable to introduce into the reaction zones and to dry out deoxyonucleoside triphosphates, forward and reverse oligonucleotide primers, probes with fluorescent labels, thermostable polymerase, and stabilizers. The stabilizers for this purpose may be chosen from polysaccharides, such as mannitol, glucose, or sucrose.

The method suggests that fluorescent identification of the change of the quantity of the polymerase chain reaction products in the samples under thermal cycling can be performed by exposing the samples to emission with a selected range of wavelengths and by registration of the fluorescence signal in the selected range of wavelengths. Fluorescence emission should be preferably performed in the range of 350-700 nm, and registration in the range of 450-1000 nm.

Then, the method provides that the microchip can be manufactured from various materials, preferably with high thermal conductivity coefficients (higher than 1 W/cm·K) and thermal diffusivity (higher than 0.6 cm$^2$/s). Such materials may include metals, such as aluminium, copper, or dielectrics, such as silicon or ceramics. Aluminium and silicon may be considered the most suitable. To ensure a small thermal mass of the microchip its size and mass should be small. The thickness of the substrate should preferably be less than 1 mm to ensure high thermal conductivity.

The method provides that the layer of the passivating material should be made of substances preventing irreversible adsorption of the PCR components and reaction inhibition. The layer should be preferably applied on the surface by covalent bonding with the material of the heat-conducting substrate of the microchip to increase the resistive properties of the passivating layer in long storage and to the thermocycling during the reaction. The substances that can be used for this purpose can be aluminium oxide, silicon oxide, and organic molecules capable of forming monolayers or polymer films. The organic molecules can be polydimethylsiloxane, polymethylmethoxysiloxane, 3-glycidoxypropyl-trimethoxysilane, and ethyleneglycol diglycidyl ether.

It is even more preferable that the passivating layer in the reaction zones should possess hydrophilic properties to guarantee good spreadability of the solution during introduction of the PCR mixture in the reaction zone. At the same time, it is preferable that the layer of the passivating material outside the reaction zones should be hydrophobic to avoid spilling of the aqueous solution beyond the borders of the reaction zone.

The most preferable variant is when the passivating material in the reaction zones should be formed as a result of the reaction of a layer of 3-glycidoxypropyl-trimethoxysilane and ethyleneglycol diglycidyl ether.

It is also preferable that the passivating materials outside the area of the reaction zones should be formed from the polymer layer of polymethylmethoxysiloxane.

Insulation of the samples from the air in the reaction zones can be achieved by applying a layer of an insulating liquid on the reaction zones. The insulating liquid should be preferably liquids immiscible with water with a density smaller than water, and with the boiling point higher than 100° C. under atmospheric pressure. The insulating liquids should be mineral oils, silicon fluids of various viscosity and their mixtures. The method provides that the insulating liquid should be transparent in the emission and registration spectral ranges of fluorescence excitation and registration of fluorescent dyes used for detection of the rt-PCR products. It is preferable that the optical transmittance of the insulating liquid in this spectral range should be not less than 10%. It is even more preferable that the insulating layer in the range of luminescent dyes registration should create a fluorescent signal not more than 10% of the signal created by the samples in the reaction zones.

The method provides that the layer of the insulating liquid can be applied both once (before or after introduction of the samples) and twice: first the layer of the insulating liquid is applied on the unfilled reaction zones, then the liquid samples are introduced through this layer of the insulating liquid and then the insulating liquid is added.

Various constructive and layout solutions of the device of the present invention are possible.

The silicon microchip of at least one reaction zone on its surface can be manufactured by photolithography with subsequent liquid anisotropic or isotropic etching that is well known to specialists in the field of microelectromechanical systems. The microchip from metal, ceramic or plastic can be manufactured by close tolerance forging, hot casting, laser ablation, liquid isotropic etching, plasma etching that are well known to specialists in this field. The dimensions of the reaction zone should be chosen from the range of $10^1$-$10^4$ μm in length and width and $10^1$-$10^3$ μm in depth. It is preferable that the dimensions of the reaction zone should be 5×$10^2$-5×$10^3$ μm in length and width, and 2×$10^2$-5×$10^2$ μm in depth.

The dimensions of the microchip should be chosen so that the thermal mass of the microchip should be small, and the thickness of the thermal conducting substrate should be minimal ensuring sufficient stability of the construction.

It is desired that the ratio of the thermal mass of the microchip with the introduced samples and the layer of the liquid immiscible with water to the thermal conductivity of the substrate be smaller than 0.04 s. For example, these conditions are satisfied by a microchip with substrate dimensions of Length×Width×Height (L×W×H) of 28×25×0.6 mm, with 16 reaction zones with the Length×Width×Depth (L×W×D) of 2×2×0.4 mm each, with a peripheral polyacrylamide barrier in the form of a rectangular frame of L×W×H of 28×25×3 mm and the border width of 4 mm.

The peripheral barrier can be made of a constructive element going above the upper surface of the microchip and forming a closed loop so that the insulating liquid should be contained in this loop in the process of the PCR. The peripheral barrier can be made of the material of the heat-conducting substrate of the microchip. It is preferable that the material for the peripheral barrier should have a low thermal conductivity coefficient and low thermal capacity. The peripheral barrier may be a layer of the material with oleophobic properties applied on the surface of the microchip around the reaction zones. The preferred materials with oleophobic properties are alkyl silanes with saturated fluorohydrocarbon chains. The peripheral barrier may be manufactured as a combination of the constructive element and a layer of oleophobic material. It is preferable that the peripheral layer should be manufactured with the possibility of insulating the reaction zones from the atmosphere by applying an adhesive film on it.

The passivating layer on the surface of the microchip covalently bound to the surface of the microchip can be obtained by chemical reactions on the surface of the microchip. These reactions can be performed by interaction of the components from the gas phase with the surface of the microchip, for example in thermochemical oxidation of silicon with formation of a silicon dioxide layer. It is preferable that these reactions should be conducted during the contact between liquid phase components and the microchip surface. The passivating material should be preferably deposited separately on the microchip surface in the reaction zones and outside these zones. It is even more preferable to apply a layer of polymethylmethoxysiloxane with hydrophobic properties on the microchip surface outside the reaction zones by contact wetting of the areas with the solution of unpolymerized polymethylmethoxysiloxane and subsequent thermal polymerization. In this case the layer of the passivating material in the reaction zones can be applied by successive chemical reactions in the reaction zones, for example, by successive incubation of liquid 3-glycidoxy-propyl-trimethoxysilane and then liquid ethyleneglycol diglycidyl ether in the reaction zones.

It is preferable that deposition of one or several components of the polymerase chain reaction in the reaction zones on the microchip surface be performed by drying out the aqueous solutions of the said components of the PCR mixture. The solutions containing the necessary components should be introduced into the reaction zones and dried out in a laminar safety hood at room temperature. It is even more advantageous to dry out these solutions using lyophilization technique, at low temperature (from −20° C. to −50° C.) and pressure (from 0.01 to 10 mm Hg).

The fluorescence detector may include an emission filtration block using absorption and interference light filters as well as dichroic mirrors. The emission source may be a light-emitting diode optically bound with the emission filtration block and the microchip by means of optical elements, lenses and mirrors, for example. According to the invention, to detect several PCR components in the same microreactor in the device it is possible to use a multi-channel detector containing several emission sources and several emission filtration filters with the possibility of switching between the sources and the emission filtration block. This multi-channel detector can be built using several light-emitting diodes, filters, and dichroic mirrors, with different spectral characteristics. It is preferable that the emission sources and emission filtration blocks should create a light flow in the chosen spectral range of fluorescence excitation in the range of 350-700 nm and should allow registration of the fluorescent signal in the selected spectral range of 450 1000 nm. The spectral ranges of fluorescence excitation and registration should be able to detect fluorescent dyes common in the PCR detection practice that are well known to specialists in this field. Examples of such dyes are: carboxyfluorescein (FAM), 6-carboxy-2',4,4',5',7,7'-hexafluorescein (HEX), 6-carboxyrhodamine (R6G), carboxy-X-rhodamine (ROX), tetramethylcarboxyrhodamine (TAMRA), 6-carboxy-4',5'-dichloro-2',7'-dimethoxyfluorescein (6-JOE), carboxyrhodamine (R110).

A fluorescence detector can be a matrix detector, a photomultiplier tube or a photodiode. According to the invention it is preferable that the radiation detector in the device should be a matrix detector, for example, a CCD-matrix (CCD is a Charge Coupling Device) or a CMOS-matrix (CMOS is Complementary Metal-Oxide-Semiconductor). In this case it is preferable that the microchip image should form on the matrix detector by means of optical elements, for example, by means of a lens, mirror-lens or reflecting objective. It is preferable that the matrix detector should allow registration of the fluorescence signal in the entire spectral range of 450-1000 nm.

The thermocycling block thermally bound to the microchip can be manufactured with the possibility of heating, cooling and maintaining the microchip temperature using resistance heaters, semiconductor thermoelectrical modules (Peltier devices), inductive heaters using energy transfer in the form of emission, heaters using thermal energy transfer by means of a liquid or gas flow, including those using condensation and evaporation. According to the invention, it is preferable that the thermocycling block in the device should be manufactured using a Peltier device as in this case there is active heating and active cooling of the microchip.

BRIEF DESCRIPTION OF THE DRAWINGS

The exemplary embodiment is illustrated by the following figures that show.

DETAILED DESCRIPTION

Figure 1:
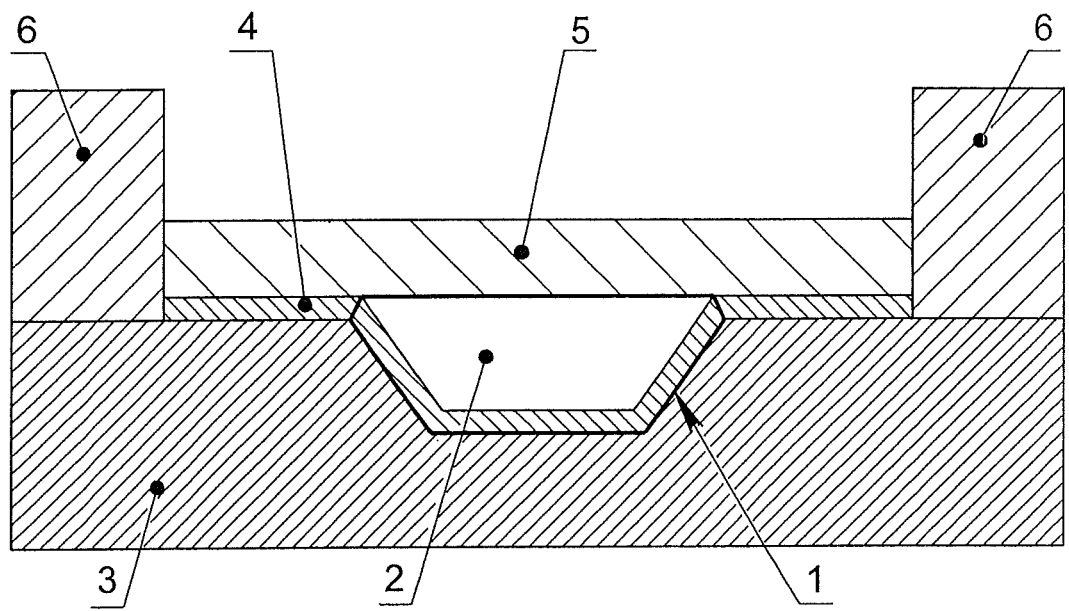
FIG. 1—the scheme of the microchip for real-time PCR analysis of nucleic acids.
Figure 2:
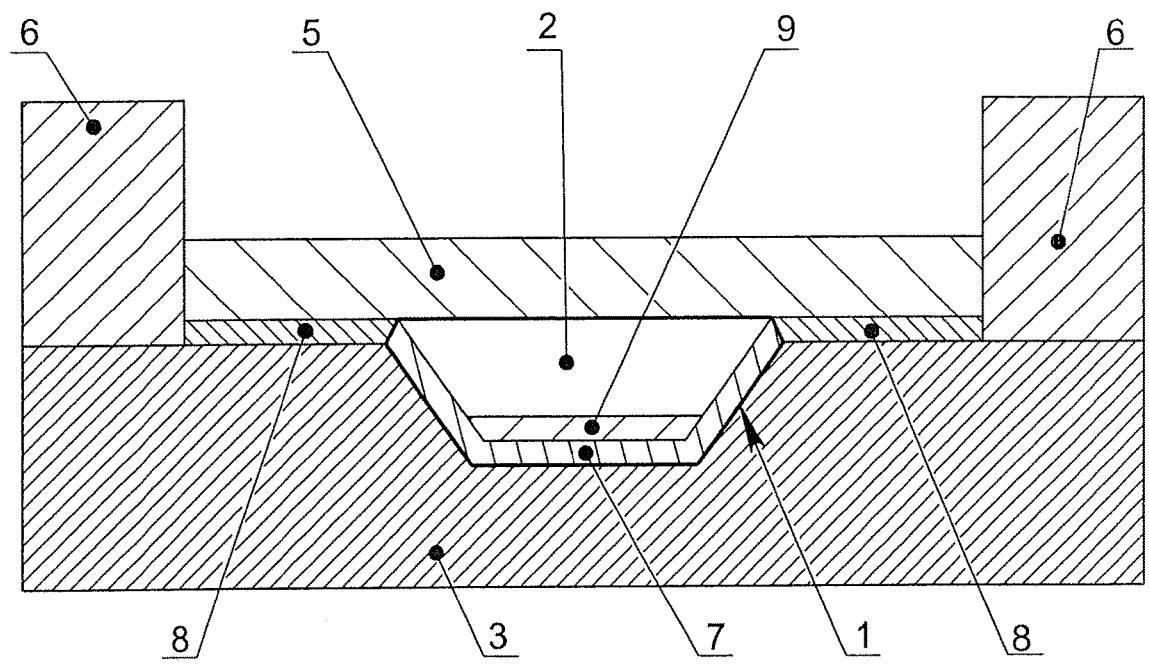
FIG. 2—a variant of the scheme for implementation of the method of real-time PCR analysis of nucleic acids with dried components of the polymerase chain reaction.

An example of microchip embodiment for implementation of the method of real-time PCR analysis of nucleic acids in accordance with the present invention is shown in FIG. 1 and FIG. 2. Sample 2 is located in the reaction zone 1 on the upper surface of the microchip. The microchip contains a heat-conducting substrate 3 made from a heat-conducting material with the thermal conductivity coefficient of more than 1 W/cm·K and the thermal diffusion coefficient of more than 0.6 cm$^2$/s.

According to the variant of the embodiment shown in FIG. 1, the reaction zone 1 is separated from the heat-conducting substrate 3 by a layer of a passivating material 4 covalently bound to the surface of the heat-conducting material.

In another embodiment shown in FIG. 2 the reaction zone 1 on the microchip surface is separated from the heat-conducting substrate 3 by a layer of a passivating material 7 with hydrophilic properties that is covalently bound to the surface of the heat-conducting material. Outside the reaction zone 1 the surface of the heat-conducting substrate 3 is covered with a layer of a passivating material 8 with hydrophobic properties that is covalently bound to the surface of the heat-conducting material. On the layer of the passivating material 8 in the reaction zone 1 there is a layer 9 containing one or several dried components of the polymerase chain reaction.

According to the variants of the embodiment shown in FIG. 1 and FIG. 2 the layer of the insulating liquid 5 separates the introduced sample 2 from the atmosphere. The peripheral barrier 6 retains the layer of the insulating liquid 5 on the upper surface of the heat-conducting substrate 3. To implement the method according to the exemplary embodiment the sample 2 containing nucleic acid is introduced into the reaction zone 1 through the layer of the insulating liquid 5. The heating and cooling of the sample 2 placed into the reaction zone is performed on the side of the lower surface of the heat-conducting substrate 3. Fluorescent evaluation of the quantity of polymerase chain reaction products in the sample 2 placed in the reaction zone 1 in the process of thermocycling is performed on the side of the upper surface of the heat-conducting substrate 3 through the layer of the insulating liquid 5.

Figure 3:
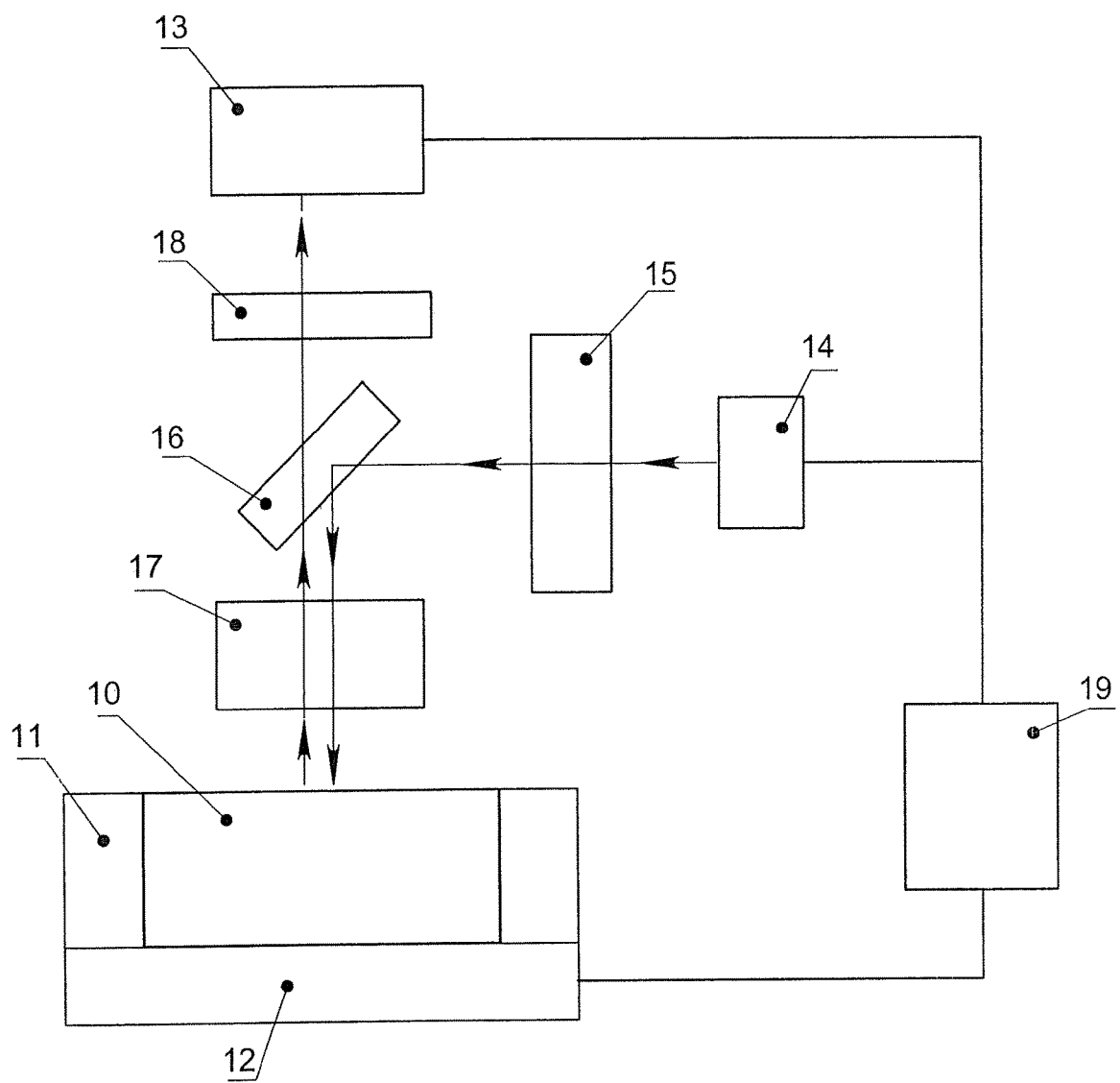
FIG. 3—an example of the scheme of design of the microchip PCR analyzer.

An example of the design of the device in accordance with the present invention is shown in FIG. 3. The device contains at least one reaction zone on the surface of the microchip 10 that is mechanically bound to the microchip holder 11, thermally bound to the thermocycling block 12 and optically bound to the fluorescence detector 13. The device contains at least one source of radiation 14 optically bound to the excitation channel spectral filtration system 15, dichroic mirror 16, lens 17 and microchip 10. The fluorescence detector 13 is optically bound to the microchip 10 via the lens 17, dichroic mirror 16 and the emission channel spectral filtration system 18. The thermocycling block 12 is manufactured with the possibility of heating, cooling and maintaining the temperature of the microchip 10. The device also contains the control system 19 electrically bound to the emission detector 13, at least with one source of emission 14 and the thermocycling block 12. The control system 19 is embodied with the possibility of switching between radiation sources 14 (if there is more than one source) as well as with the possibility of changing the spectral range of the spectral filtration system (or systems).

The device operates in the following way. The microchip 10 is inserted into the microchip holder 11. The upper surface of the microchip 10 is covered with a layer of the insulating liquid 5 and the sample 2 is introduced through it into the reaction zone 1. The microchip holder 11 with the equipped microchip 10 is then installed in the thermocycling block 12. Radiation from the radiation source 14 is directed to the excitation channel spectral filtration system 15, is then reflected from the dichroic mirror 16, gets into the lens 17 and then on the sample 2 located in the reaction zone of the microchip 1 through the layer of the insulating liquid 5. The fluorescent radiation from the sample through the layer of the insulating liquid 5 is collected by the lens 17 and directed through the dichroic mirror 16 and the emission channel spectral filtration system 18 to the fluorescence detector 13. The thermocycling block 12 thermally bound to the microchip 10 supplies and removes heat for heating, cooling and maintaining the temperature of the microchip 10. The high heating and cooling rates are achieved due to the small aggregate thermal mass of the microchip with introduced samples and the layer of the liquid immiscible with water (in the range from 0.5 to 4 J/K) embodied with the possibility of using the heat-conducting substrate with a high thermal conductance (in the range of 100-500 W/K), which results in a small ratio of the aggregate thermal mass of the microchip to thermal conductance of the substrate of the microchip (in the range of 0.001-0.04 s). The temperature conditions of the thermocycling block 12, the selection and activation of the radiation source 14 as well as collection and processing of the signals of the fluorescence detector 13 during the sample thermocycling are controlled by a control system 19 electrically bound to blocks 12, 13 and 14.

Information Confirming the Possibility of Implementation of the Invention.

The Invention is Illustrated by the Following Examples.

The description of these examples must not be used to restrict the claims of this patent; it just illustrates the possibility for the specialists in this field to implement the invention.

Example 1

The microchip containing 16 reaction zones on its surface was manufactured from polished silicon wafers 0.6 mm thick using the photolithography method with subsequent anisotropic wet chemical etching. The dimensions of the heat-conducting substrate were 25×28×0.6 mm. The reaction zones were located on the surface of the microchip as a matrix of 4×4. Every reaction zone had a shape of a frustum of a pyramid, with the dimensions of the upper base of 2×2, lower base of 1.7×1.7 mm and the depth of 0.4 mm. The whole area of the silicon substrate was covered by silicon dioxide $SiO_2$ by thermochemical oxidation. The silicon substrate covered with the silicon dioxide was cleaned in a mixture of concentrated sulfuric acid and hydrogen peroxide (3:1) during 20 minutes. After thorough washing with demi deionized water and drying the surface of the silicon substrate outside the reaction zones was treated with polymethylmethoxysiloxane "Penta-111" (Penta-North, Russia). After polymerization in the thermal treatment the surface of the reaction zones was treated first with 3-glycidoxypropyl-trimethoxysilane (Sigma, USA) for 60 minutes and then with ethyleneglycol diglycidyl ether (Sigma, USA) for 60 minutes. This substrate then was glued to the 3 mm thick peripheral polyacrylate barrier.

According to the calculations, the total thermal mass of the microchip with the samples of the reaction zones and the insulating liquid was estimated at 3.35 J/K. The thermal conductance of the silicon substrate was estimated at 175 W/K. At the same time, the ratio of the total thermal mass of the microchip to the thermal conductivity of the microchip substrate did not exceed 0.02 s.

The microchip was treated by UV radiation during 5 minutes with subsequent coverage of the upper surface of the peripheral barrier by a protective polymeric film to prevent contamination of the surface of the reaction zones during microchip storage and handling. In this way the microchip could be stored at room temperature for several months.

According to the exemplary embodiment the light emitting diodes XL9030 (Cree, USA) served as the emission sources in the device, CCD camera MultiBlue (Perkin-Elmer Optoelectronics, USA)—as a detector, XF-52 interference light filters (Omega Optical, USA)—in the emission filtration block. The Peltier device (40W, Cryotherm, Russia) was used in the thermocycling block and a personal computer with installed software was used as the control system.

The following solutions were prepared for real-time PCR:

1) amplification mixture containing:

80 mM Tris-HCl (pH=8.0), 0.1% Triton X-100, 5% glycerol (Sigma, USA), 5 mM $MgCl_2$, 24 mM $(NH_4)_2SO_4$, 0.5 mM EDTA, deoxyonucleoside triphosphates dATP, dTTP, dGTP, dCTP of 500 µM each, OligoTaq DNA-polymerase 0.1 U/µl (Promega, USA); forward and reverse oligonucleotide primers in the concentration of 0.5 µM, fluorescently labeled oligonucleotide probe in the concentration of 0.2 µM for detection of *Escherichia coli*, strain C600, gene fragment 16S pRNA, sterile deionized water.

2) sample solution containing $10^4$ DNA of *Escherichia coli* copies in 1 µl, strain C600, in sterile deionized water (sample K+). Sterile deionized water (sample K−) was used as the sample not containing specific DNA.

The freshly prepared solutions were mixed in the ratio of 1:1, mixed by a vibration mixer and pipetting and then centrifuged. The obtained working PCR mixture was used for introduction into the reaction zones of the microchip.

The covering isolating layer consisted of 100 µL of silicon liquid PMS-200 (Penta-North, Russia) was introduced on the upper surface of the microchip limited by the peripheral barrier by means of a micropipette. The liquid served as the insulating liquid. Through this isolation layer 2 μL of the PCR working mixture was introduced by means of a micropipette. The mixture easily dispersed into the reactions zones, did not spread on the substrate surface thus preventing mutual contamination due to hydrophilic surface properties in the reaction zones and hydrophobic properties of the surface outside the reaction zones.

Thermocycling was performed in the temperature conditions recommended by the manufacturer of the reactants: polymerase activation at 94° C. during 180 sec (1 cycle), DNA denaturation at 94° C. during 20 sec, primer annealing at 58° C. during 40 sec, elongation of amplicons and fluorescence signal pickup at 72° C. during 20 sec (45 cycles).

Figure 4:
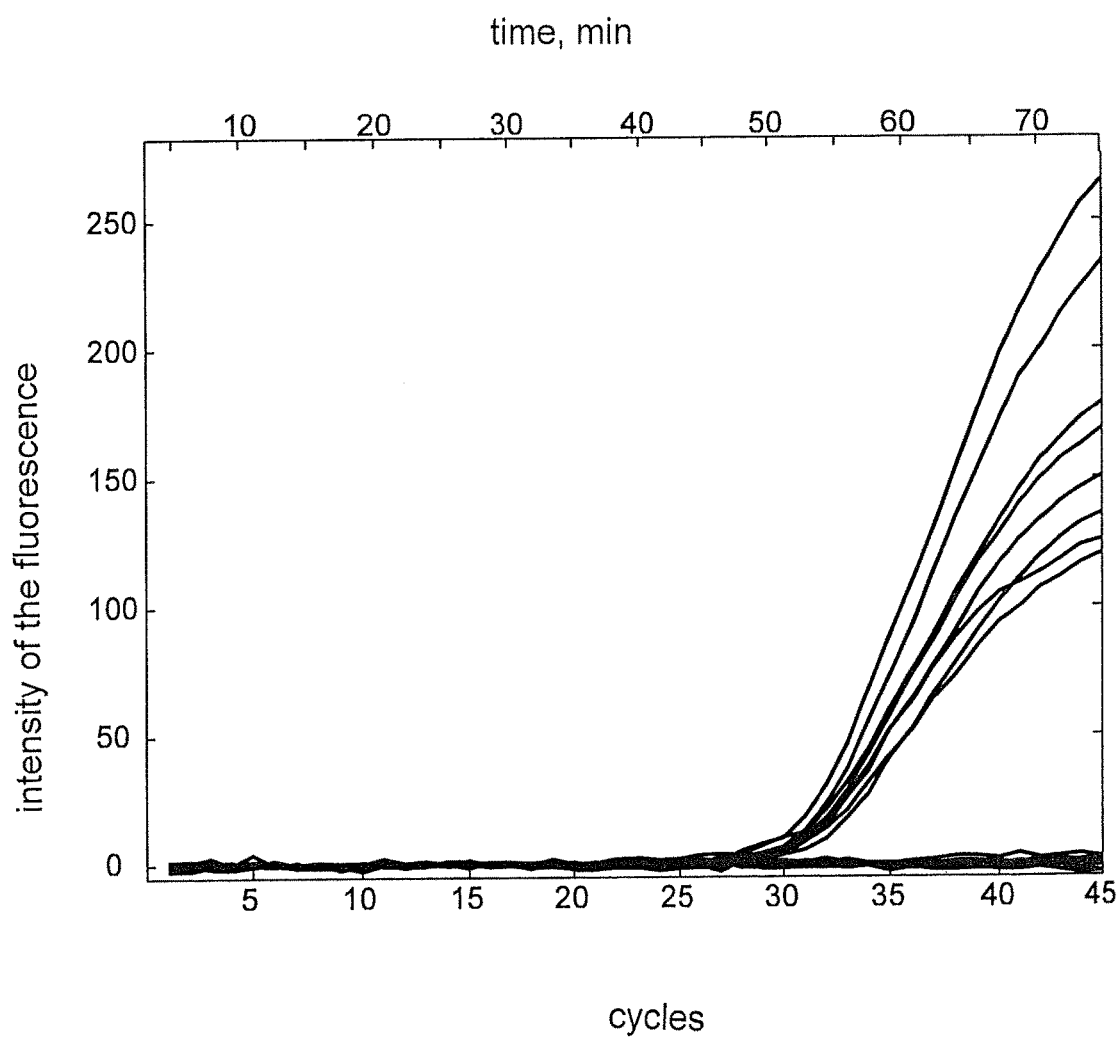
FIG. 4—the result of DNA identification by real-time PCR analysis using the device according to the invention in using the temperature conditions recommended by the manufacturer of the reactants.

The result of the rt-PCR analysis is shown in FIG. 4. It is typical of rt-PCR curves that at the initial stages the intensity of fluorescence is small and practically does not change. This level of fluorescence is called the baseline level. The indicator of the accumulation of the reaction product is the so-called "threshold cycle", i.e. the cycle in which the intensity of the fluorescence starts exceeding the baseline level. FIG. 4 shows that the samples containing the DNA of interest exhibit an increase in fluorescence signal while fluorescence from the samples that do not contain this DNA stays at the baseline level.

Comparison of the average value of the threshold cycles (Ct) obtained in the present example f solutions using the device in accordance with the invention (Ct=31.3) and the threshold cycles obtained using the commercially available instrumentation SmartCycler II (Cepheid, USA) with fully analogous thermocycling conditions (Ct=31.0) shows that the analytical characteristics of the device according to the invention and the commercially available equipment are comparable.

At the same time the maximum rates of heating and cooling for the device according to the invention were 16.5 and 14.3° C./s, correspondingly, which were 4 and 8 times higher, respectively, compared to commercially available instrumentation, and 2 and 5 times higher compared to the fastest samples of the commercially available equipment.

The time spent in the present example to achieve the threshold cycle using the device according to the invention was 53.1 min.

Example 2

The microchip and the device according to the invention were similar to those described in example 1.

The solutions prepared for the rt-PCR were similar to example 1. Preparation of the working PCR mixture and its introduction in the reaction zones of the microchip were performed in the way similar to example 1.

Thermocycling was performed in the temperature conditions with reduced duration of the stages of denaturation, primer annealing and elongation: polymerase activation at 94° C. during 120 s (1 cycle), DNA denaturation at 94° C. during 3 s, primer annealing at 58° C. during 3 s, elongation of amplicons and fluorescence signal pickup at 72° C. during 8 s (45 cycles).

Figure 5:
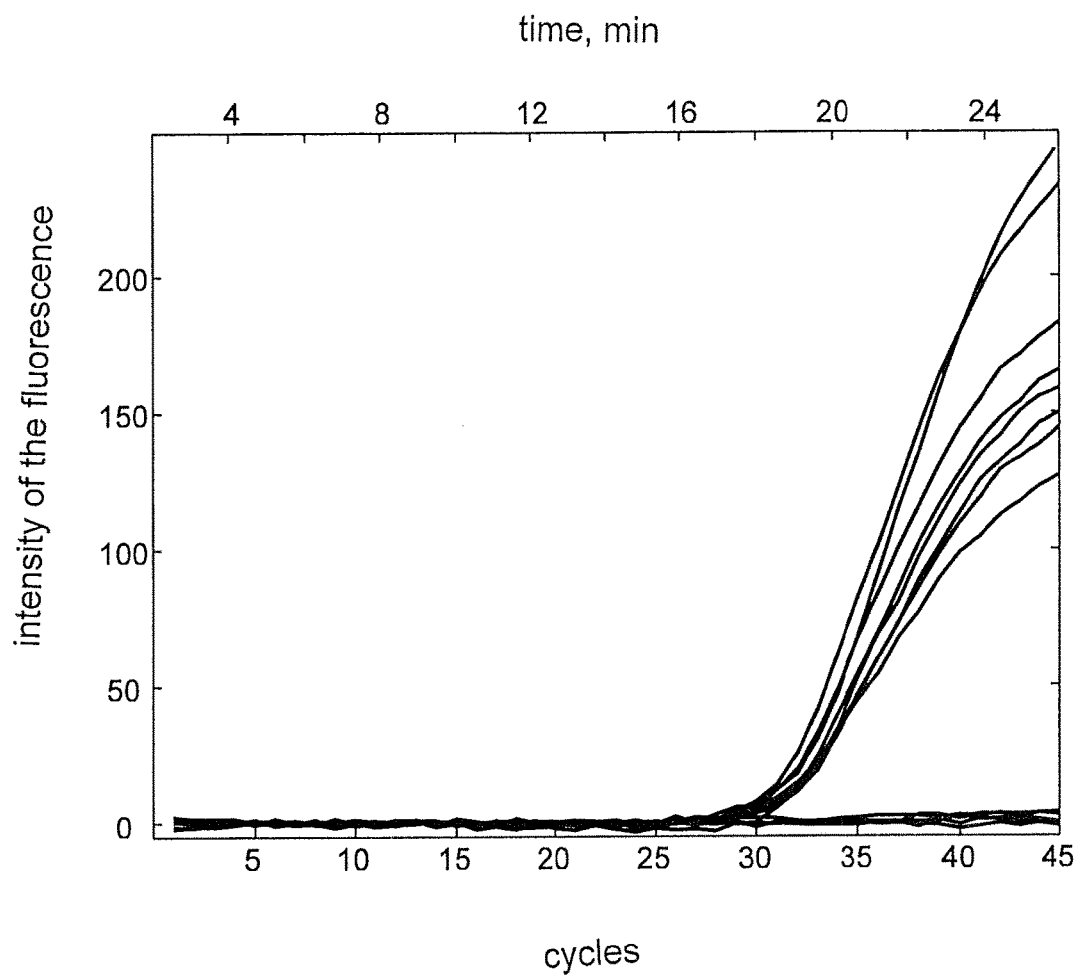
FIG. 5—the result of DNA identification by real-time PCR analysis using the device according to the invention in using the temperature conditions with shortened duration of PCR stages.

The result of the example is shown in FIG. 5. The figure shows that the samples containing the DNA under investigation exhibit increase in the fluorescence signals while the samples that do not contain this type of DNA do not show the increase of the fluorescence signal. Comparison between the threshold cycles (Ct) obtained using the device according to the exemplary embodiment with the temperature conditions recommended by the manufacture of the test-systems Ct=31.3 and using the temperature conditions with shortened duration of the PCR stages Ct=31.9 shows that the effectiveness of the PCR reaction in the shortened temperature conditions changes insignificantly.

The time to reach the threshold cycle in the present example was only 18 min using the device according to the invention, which is 3 times faster compared to the use of one of the fastest commercially available PCR analyzers Smart Cycler II (54.7 min).

Example 3

The microchip and the device according to the invention were similar to those described in example 1.

The following solutions were prepared for the rt-PCR:

1) amplification mixture containing 80 mM Tris-HCl (pH=8.0), 0.1% Triton X-100, 24 mM $(NH_4)_2SO_4$, 0.5 mM EDTA, deoxyonucleoside triphosphates dATP, dTTP, dGTP, dCTP of 500 μM each, 0.16% D-glucose, 1.6% inuline, 8% D-mannitol (Sigma, USA), OligoTaq DNA-polymerase 0.1 U/μl (Promega, USA); forward and reverse primers in the concentration of 0.5 μM, fluorescently labeled oligonucleotide probe in the concentration of 0.2 μM for detection of the DNA of *Escherichia coli*, strain C600, gene fragment 16S pRNA, sterile deionized water.

2) sample solution containing $10^4$ DNA of *Escherichia coli* copies in 1 μl, strain C600, in sterile deionized water (sample K+) or sterile deionized water (sample K−) in the solution containing 5 mM $MgCl_2$, 10 mM Tris-HCl (pH=8.0), 0.1% Triton X-100, 5% glycerol (Sigma, USA) and sterile deionized water.

1 μl of amplification mixture prepared according to item 1 of the present example was introduced into each of the 16 reaction zones of the microchip. The mixture was dried out in a laminar flow hood at room temperature during 2-3 hours until a dense layer firmly retained in the reaction zones was formed. The upper surface of the peripheral barrier was coated by a protective polymeric film with an adhesive layer isolating the reaction zones from the atmosphere to prevent contamination of the surface of the reaction zones during microchip storage and handling. In this way the microchip could be stored at room temperature for several weeks.

For the PCR analysis the solution of the sample according to item 2 of the present example was introduced into the reaction zones of the microchip in the way similar to example 1.

Thermocycling was performed in the temperature conditions recommended by the manufacturer of the reactants: polymerase activation at 94° C. during 180 s (1 cycle), DNA denaturation at 94° C. during 20 s, primer annealing at 58° C. during 40 s, elongation of amplicons and fluorescence signal pickup at 72° C. during 20 s (45 cycles).

As result rt-PCR curves were obtained (no data are available) that show that the samples containing the target DNA exhibit increased fluorescence signal while the samples that do not contain the target DNA the fluorescence signal does not increase. The experiment identified that the quantity of the consumables, labour costs and time spent on performance of preparatory operations for sample preparation and introduction of the obtained mixtures into the reaction zones decreased considerably with use of the method and the device according to the present invention compared to conventional equipment. For example, the quantity of PCR reagents dropped 12 times, the quantity of the dose-meter tips decreased 6 times, the quantity of pipetting stages decreased twice, the time required for preparatory operations dropped 4 times.

The important advantages of the exemplary embodiment resulting in achievement of the set task may be said to be:
1. increased rate of the sample thermocycling due to use of materials with high thermal conductivity as well as due to the contact of the sample with the surface of the reaction zone;
2. elimination of PCR inhibition due to the passivating layer of the surface of the reaction zones, which increases sensitivity, accuracy and reliability of the analysis;
3. reduced labour intensity and cost of the PCR analysis due to use of the microchip containing dried PCR reagents.

Given above are preferred examples of the invention implementation that do not restrict the essence and limits of the invention but just illustrate it. Specialists in this field will easily find various modifications and improvements of the proposed invention that also come within its scope reflected in the claim of the invention.

The invention claimed is:

1. A device for identification of nucleic acids by a method of real-time polymerase chain reaction comprising:
   a microchip;
   a microchip holder;
   a fluorescence detector, wherein the microchip includes a surface with at least one reaction zone, wherein the reaction zone is mechanically bound to the microchip holder and optically bound to the fluorescence detector via an emission channel spectral filtration system;
   at least one radiation source, wherein the at least one radiation source is optically bound to at least one excitation channel spectral filtration system and the microchip; and
   a control system, wherein the control system is electrically bound to a thermocycling block, wherein the thermocycling block is thermally bound to the microchip and is manufactured to heat, cool and maintain the microchip temperature,
   wherein the microchip contains a heat-conducting substrate thermally bound to the thermocycling block and made of aluminum with a thermal conductivity coefficient of more than 1 W/cm·K and a thermal diffusivity coefficient of more than 0.6 $cm^2$/s,
   wherein each reaction zone is separated from the heat-conducting substrate by a layer of a passivating material comprised of silicon oxide and aluminum oxide covalently bound to the surface of the heat-conducting substrate, wherein one or several dried components of the polymerase chain reaction is placed over the layer of the passivating material,
   wherein an upper surface of the microchip has a peripheral barrier, wherein the peripheral barrier is configured to retain an assigned quantity of a liquid immiscible with water on an upper surface of the microchip, and
   wherein the ratio of the aggregate thermal mass of the microchip with introduced samples and the layer of the liquid immiscible with water, to thermal conductance of the microchip substrate does not exceed 0.04 seconds.

2. The device according to claim 1, wherein the at least one radiation source includes at least one light-emitting diode.

3. The device according to claim 1, wherein the at least one radiation source includes a matrix of light-emitting diodes.

4. The device according to claim 3, wherein the fluorescence detector includes a photoelectron multiplier.

5. The device according to claim 3, wherein the fluorescence detector includes a photodiode.

6. The device according to claim 1, wherein the control system is configured to switch radiation sources between each other.

7. The device according to claim 1, wherein the control system is configured to change the spectral range of the at least one spectral filtration system.

8. The device according to claim 1, wherein the fluorescence detector includes a matrix detector.

9. The device according to claim 1, wherein the thermocycling block includes a Peltier device.

10. The device according to claim 1, wherein the microchip is configured so that the surface of the microchip in the reaction zones is covered by a layer of a hydrophilic passivating material and the surface of the microchip between the reaction zones is covered by a hydrophobic passivating material.

11. The device according to claim 1, wherein the peripheral barrier is configured to isolate the reaction zones from the atmosphere by an adhesive film.

12. The device according to claim 1, wherein the control system is configured to automatically switch the radiation sources and spectral filtration systems while collection of signals from the fluorescence detector is synchronized with these switches.

13. The device according to claim 1, wherein the layer of the passivating material is configured to prevent irreversible adsorption of the PCR components and reaction inhibition.

14. A device for identification of nucleic acids by a method of real-time polymerase chain reaction comprising:
   a microchip;
   a microchip holder;
   a fluorescence detector, wherein the microchip includes a surface with at least one reaction zone, wherein the reaction zone is mechanically bound to the microchip holder and optically bound to the fluorescence detector via an emission channel spectral filtration system;
   at least one radiation source, wherein the at least one radiation source is optically bound to at least one excitation channel spectral filtration system and the microchip; and
   a control system, wherein the control system is electrically bound to a thermocycling block, wherein the thermocycling block is thermally bound to the microchip and is manufactured to heat, cool and maintain the microchip temperature,
   wherein the microchip contains a heat-conducting substrate thermally bound to the thermocycling block and comprised of aluminum,
   wherein each reaction zone is separated from the heat-conducting substrate by a layer of a passivating material comprised of silicon oxide and aluminum oxide covalently bound to the surface of the heat-conducting substrate, wherein the layer of passivating material is configured to have one or several dried components of the polymerase chain reaction placed over the layer of the passivating material,
   wherein an upper surface of the microchip has a peripheral barrier, wherein the peripheral barrier is configured to retain an assigned quantity of a liquid immiscible with water on an upper surface of the microchip, and
   wherein the layer of the passivating material is configured to prevent irreversible adsorption of the PCR components and reaction inhibition.

15. The device according to claim 14, wherein the surface of the microchip between the reaction zones is covered by a layer of polymethylmethoxysiloxane with hydrophobic properties.

16. The device according to claim 14, wherein the fluorescence detector includes an emission filtration block, wherein the emission filtration block includes absorption and interference light filters and dichroic mirrors.

17. The device according to claim 14 further including a plurality of radiation sources, wherein the fluorescence detector includes a plurality of emission filtration blocks, wherein the radiation sources and emission filtration blocks are configured to create a light flow in the chosen spectral range of fluorescence excitation in the range of 350-700 nm and allow registration for the fluorescent signal in the selected spectral range of 450-1000 nm.

18. The device according to claim 14, wherein the passivating material in the reaction zones is formed by the reaction of a layer of 3-glycidoxypropyl-trimethoxysilane and ethyleneglycol diglycidyl ether.

19. The device according to claim 14 and further including passivating material outside the area of the reaction zones, wherein the passivating material outside the area of the reaction zones is formed from a polymer layer of polymethylmethoxysiloxane.

20. The device according to claim 14, wherein the insulating liquid is transparent in the emission and registration of spectral ranges of fluorescence excitation and registration of fluorescent dyes used for detection of rt-PCR products.

21. The device according to claim 14, wherein the peripheral barrier includes a layer of material with oleophobic properties applied on the surface of the microchip around the reaction zones.

22. The device according to claim 21, wherein the layer of material of the peripheral barrier includes alkyl silanes with saturated fluorohydrocarbon chains.

23. The device according to claim 14, wherein the liquid immiscible with water is silicon liquid.

24. A method of identification of nucleic acids by a real time polymerase chain reaction
using a device including
a microchip;
a microchip holder;
a fluorescence detector, wherein the microchip includes a surface with at least one reaction zone, wherein the at least one reaction zone is mechanically bound to the microchip holder and optically bound to the fluorescence detector via an emission channel spectral filtration system;
at least one radiation source, wherein the at least one radiation source is optically bound to at least one excitation channel spectral filtration system and the microchip; and
a control system, wherein the control system is electrically bound to a thermocycling block, wherein the thermocycling block is thermally bound to the microchip and is manufactured to heat, cool and maintain the microchip temperature,
wherein the microchip contains a heat-conducting substrate thermally bound to the thermocycling block and made of aluminum with a thermal conductivity coefficient of more than 1 W/cm·K and a thermal diffusivity coefficient of more than 0.6 cm²/s,
wherein each reaction zone is separated from the heat-conducting substrate by a layer of a passivating material comprised of silicon oxide and aluminum oxide covalently bound to the surface of the heat-conducting substrate,
wherein an upper surface of the microchip has a peripheral barrier, wherein the peripheral barrier is configured to retain an assigned quantity of a liquid immiscible with water on an upper surface of the microchip,
the method comprising:
a) placing one or several dried components of samples for the polymerase chain reaction over the layer of the passivating material in the at least one reaction zone of the device,
b) introducing liquid samples for the polymerase chain reaction containing nucleic acid into the at least one reaction zone,
c) isolating the samples in the at least one reaction zone from atmosphere wherein the samples are isolated by separating them from atmosphere by layer of liquid immiscible with water that is retained on the upper surface of the microchip by the peripheral barrier, wherein the ratio of the aggregate thermal mass of the microchip with introduced samples and the layer of the liquid immiscible with water to the thermal conductance of the microchip substrate does not exceed 0.04 seconds,
d) thermocycling the samples through the microchip heating, cooling and maintaining microchip temperature,
e) detecting change of the quantity of polymerase chain reaction products in the samples during thermocycling in (d) through detection of fluorescent change using the at least one radiation source of the device to expose the samples to radiation and the fluorescence detector of the device to produce a fluorescence signal,
f) identifying an initial quantity of the nucleic acid of the samples by dynamic growth of the fluorescence signal.

25. The method according to claim 24, wherein (e) includes exposing the samples to radiation with a selected spectral range of 350-700 nm and detecting the fluorescence signal in a selected spectral range of 450-1000 nm.

26. The method according to claim 24, wherein in (b) the liquid samples are introduced into the at least one reaction zone though the layer of the liquid immiscible with water.

27. The method according to claim 24, wherein in (a) the passivating material on the surface of the microchip in the at least one reaction zone is a hydrophilic material, and wherein the device includes a hydrophobic passivating material on the microchip surface between reaction zones.

28. The method according to claim 24, wherein in (c) the layer of a liquid immiscible with water has a transmission rate in a selected spectral range of radiation and in a selected spectral range of fluorescence of at least 10%.

29. The method according to claim 24, wherein in (c) the layer of a liquid immiscible with water has an associated fluorescence signal not exceeding 10% of the fluorescence signal created by the samples placed in the at least one reaction zone.

30. The method according to claim 24, wherein in (c) the liquid immiscible with water is a polymethylmethoxysiloxane liquid with density below the density of water.

31. The method according to claim 24, wherein in (a) the layer of the passivating material is operative to prevent irreversible adsorption of polymerase chain reaction components and polymerase chain reaction inhibition.

* * * * *